United States Patent [19]

Terranova et al.

[11] Patent Number: 4,702,734
[45] Date of Patent: Oct. 27, 1987

[54] METHOD OF PROMOTING PERIODONTAL REGENERATION AND FIBROBLAST BONDING

[75] Inventors: Victor P. Terranova, Gaithersburg, Md.; Ulf M. E. Wikesjo, Williamsville; Robert J. Genco, Buffalo, both of N.Y.; Susanne Hic, Washington, D.C.; Raymond M. Lyall, Gaithersburg, Md.

[73] Assignee: Meloy Laboratories, Inc., Springfield, Va.

[21] Appl. No.: 861,195

[22] Filed: May 8, 1986

[51] Int. Cl.$^4$ ............................................. A61M 31/00
[52] U.S. Cl. ........................................ 604/54; 604/77
[58] Field of Search .................. 128/1 R; 604/54, 55, 604/77; 433/80

[56] References Cited

PUBLICATIONS

"Chemical Treatment of Diseased Root Surfaces in Vitro", Wirthlin et al, Journal Periodontology, vol. 52, No. 11, Nov. 1981, pp. 694-696.
"Fibronectin Mediated Human Gingival Fibroblasts Attachment to Bone", Arisawa et al, General Pharmacology, vol. 15, No. 4, pp. 293-299, 1984.
The Merck Index, pp. 1315, 1316 (9021), 1984.
"The Effect of Citric Acid and Fibronectin Application on Healing Following Surgical Treatment of Naturally Occurring Periodontal Disease in Beagle Dogs", Caffesse et al, Journal of Clinical Periodontology, vol. 12, 8/1985, pp. 578-590.
"Attachment, Growth and Synthesis by Human Gingival Fibroblasts on Demineralized or Fibronectin--Treated Normal and Diseased Tooth Roots", Fernyhough et al., Journal of Periodontology, Mar. 1983, pp. 133-139.

Primary Examiner—C. Fred Rosenbaum
Assistant Examiner—J. L. Kruter

[57] ABSTRACT

This invention relates to a method for promoting periodontal regeneration in humans, the method comprising
(a) application of an agent which demineralizes enamel and dentin, and subsequently
(b) application of an agent which stimulates the formulation of endothelial cells.

2 Claims, No Drawings

4,702,734

METHOD OF PROMOTING PERIODONTAL REGENERATION AND FIBROBLAST BONDING

FIELD OF THE INVENTION

The present invention relates to a method of promoting periodontal regeneration and a kit for use in the method.

BACKGROUND OF THE INVENTION

Present modalities for the treatment of periodontal diseases arrest their progression, but have only minimal potential to regenerate the supporting apparatus of the tooth. For example, periodontal disease as an infection can be arrested by use of specific antimicrobial agents (Genco 1981). Recent research has focused on development of predictable procedures aimed at obtaining new connective tissue attachment to previously diseased tooth root surfaces (for review see Selvig 1983, Nyman, Lindhe & Karring 1983). One approach has used mechanical modulation to select for cells of mesenchymal origin (Nyman et al. 1982a, b, Aukhil, Simpson & Schaberg 1983, Gottlow et al. 1984). Another approach has used partial demineralization of the root dentin surface with saturated citric acid to enhance mesenchymal cell adhesion (Register & Burdick 1976, Crigger et al. 1978, Cole et al. 1980, Klinge et al. 1981). Citric acid treatment of the dentin exposes collagen fibrils (Garrett, Crigger & Dgelberg 1978, Boyko, Brunette & Melcher 1980, Heritier 1982), thus offering a possible biochemical mechanism for increased cell adhesion. Unfortunately, the initial healing observed following either approach is often hampered by irreversible resorption and ankylosis of the root (Aukhil, Simpson & Schaberg 1983, Magnusson et al. 1985, Bogle, Claffey & Egelberg 1985).

It would be desirable to have a method to regenerate periodontal tissue.

SUMMARY OF THE INVENTION

This invention relates to a method for promoting periodontal regeneration in humans, the method comprising (a) application of an agent which demineralizes enamel and dentin, and subsequently (b) application of an agent which stimulates the formulation of endothelial cells.

This invention also relates to a kit comprising (a) tetracycline in a pharmaceutically acceptable dosage form for administration to teeth, and (b) fibronectin in a pharmaceutically acceptable dosage form for administration to the teeth.

DETAILED DESCRIPTION OF THE INVENTION

A. Agents which demineralize enamel and dentin.

Those agents include citric acid and its salts and tetracycline and its salts. Preferred is the use of tetracycline HCl in the present invention.

Tetracycline HCl is substantive, binding to enamel, while retaining its antimicrobial activity. Aqueous solutions of tetracycline HCl have been shown to partially demineralize enamel and dentin.

Surface demineralization of dentin with tetracycline HCl enhances binding of fibronectin and fibroblasts to surfaces over that observed with citric acid, partially demineralized dentin and untreated controls. Furthermore, tetracycline partially demineralized dentin binds less laminin and this subsequently inhibits attachment of epithelial cells. Root surface conditioning with a demineralizing agent facilitates healing of the hard/soft tissue interface. This improved healing may result by providing a suitable root surface as substrate for mesenchymal cells, and by the antimicrobial activity of tetracycline HCl. The following are the results of testing to evaluate conditioning of denture surfaces with tetracycline.

Method

Dentin slabs were prepared from roots of freshly extracted bovine teeth. The slabs (8×4×mm) were cut with a water-cooled diamond saw (Hamco), followed by conditioning with 600 mesh sandpapers to obtain a surface whose qualities resemble those following clinical root instrumentation (Glantz 1969). The slabs were sterilized by gamma irradiation ($5.0 \times 10^5$ rads) while immersed in distilled water.

To study adsorption of tetracycline HCl, dentin slabs were immersed in 250 ul of 10, 25, 50, and 100 mg/ml aqueous solutions of $^3$H-tetracycline HCl for 5 minutes at 37° C. Next followed a vigorous rinse in 5 ml of phosphate buffered saline at pH 7.4 for 5 minutes. Adsorbed radioactive tetracyclinc HCl was quantitated by liquid scintillation counting after dissolving the dentin slab in 5.0 ml of 2 N HCl.

Desorption of tetracycline HCl from dentin was measured by monitoring tritium release from dentin slabs treated with a 50 mg/ml solution of $^3$H-tetracycline HCl. The duplicate $^3$H-tetracycline HCl exposed dentin slabs were placed in Eppendorf tubes into which 250 ul of media (Minimal Essential Medium plus 10% fetal bovine serum) was added. At 20 minute intervals over a period of 48 hours, 100 ul samples were removed and radioactive tetracycline measured. The same amount of fresh medium was added to the well immediately after removal of the sample to simulate tissue fluid flow and to maintain a constant incubation volume.

Inhibition of bacterial growth by dentin previously immersed in tetracycline HCl was determined using the assay of Evans et al. (1977). Slabs were pretreated for 2 hours at 37° C. in distilled water (control), serum, whole blood, or filter-sterilized (0.45 u pore size) whole saliva (all obtained from the same healthy donor). Slabs were next rinsed 5 minutes in sterile saline (0.9% NaCl). Each slab was immersed in 250 ul of an aqueous solution of tetracycline HCl at 1.2, 3.7, 11 or 33 ug/ml for 5 minutes at room temperature, after which they were rinsed for 5 minutes in 5 ml of sterile saline and placed in a culture tube containing 1 ml of sterile trypticase-yeast extract medium supplemented with 1% sucrose. The tubes were then inoculated with 50 ul of an overnight culture of *Actinomyces naeslundii* ATCC 12104, and incubated overnight in an anaerobic chamber (Forma) in an atmosphere of 5% $CO_2$, 10% $H_2$ and 85% $N_2$. Bacterial growth was assessed by spectrophotometric measurement of the turbidity of the dentin-adherent, glass-adherent, and non-adherent fractions at 540 nm. Total growth was calculated from the sum of the optical densities of the three fractions. Inhibition at each concentration of tetracycline HCl in which the slabs were immersed, was calculated by comparison of the optical density of test slabs to that of control slabs which had been treated identically except that they were immersed in distilled water for 5 minutes rather than in tetracycline HCl.

The morphological effects of tetracycline HCl on dentin were determined by comparing the surfaces of control slabs to those pretreated with distilled water or biological fluids and then exposed to tetracycline HCl and rinsed as described above. Slabs were fixed for 2 hours at 4° C. in 2% gluteraldehyde buffered at pH 7.2 with 0.2M cacodylate. The slabs were then postfixed in 1% $OsO_4$ and dehydrated through a graded ethanol series. Slabs were then dried by the critical point method (Ladd), coated with gold (Edwards) and observed in a scanning electron microscope (Hitachi).

Results

Adsorption of $^3H$-tetracycline HCl to bovine dentin slabs was found to be maximal when the slabs were immersed in 50 mg/ml of $^3H$-tetracycline HCl. This resulted in adsorption of 410±40 ug tetracycline HCl per dentin slab, or 4.7 ug/mm$^2$.

The kinetics of desorption into tissue culture medium containing 10% serum was as follows. At time 0, tetracycline HCl in the medium was 20±3 ug/ml. During the first two hours the desorbed tetracycline HCl reached 100 ug/ml, and the concentration decreased over time. After 48 hours the concentration of desorbed $^3H$-tetracycline HCl was still at 4.2 ug/ml.

The antimicrobial activity of the tetracycline HCl released from dentin was that maximal inhibition of bacterial growth (mean 98±1%) was achieved with slabs treated with between 11 and 33 ug/ml tetracycline HCl. The $ID_{50}$s obtained by probit analysis (Evans et al. 1977) were: 3.3 ug/ml for distilled water pretreatment, 2.4 ug/ml for serum, 3.7 ug/ml for blood, and 5.9 ug/ml for saliva. These values did not differ among the pretreatment conditions since they overlapped at the 95% confidence level suggesting that the various pretreatment conditions did not affect either the adsorption or the subsequent release of active tetracycline from the slabs. Growth of the dentin-adherent and total bacteria was inhibited to the same extent, suggesting that the inhibitory effects measured resulted from release of active tetracycline HCl into the media.

Substantivity, defined as the percentage of active tetracycline HCl desorbed from the dentin, to the $ID_{50}$s obtained by a separate broth macrodilution assay in which tetracycline HCl was added directly to the medium. The tetracycline bound and subsequently released was 2-4% of the originally applied dose at immersion concentrations ranging from 1.2-33 ug/ml.

The surface morphology of dentin was next evaluated by scanning electron microscopy. The surfaces of untreated slabs presented an irregular coating, previously defined as a smear layer (Jones, Lozdan & Doyde 1972). Few dentin tubule openings were visible and these were partially obturated. Pretreatment of the specimens with serum did not significantly alter these features. Pretreatment of the dentin with whole blood or whole saliva yielded results similar to those observed with serum. Immersion of dentin in 10 or 100 mg/ml solutions of tetracycline HCl removed the smear layer and exposed a regular pattern of open dentin tubules. Furthermore, the changes observed after tetracycline HCl treatment were the same regardless of pretreatment. The surface morphology did not differ when distilled water, serum, blood or saliva were used to pretreat the slabs. Dentin slabs treated with saturated citric acid demonstrated similar surface morphology to those treated with tetracycline HCl.

Conclusion

The studies show that tetracycline HCl conditioning of root dentin results in substantial binding of biologically active concentrations of tetracycline HCl, removal of the smear layer, and exposure of the dentin tubules.

Besides its well known antimicrobial activity and the substantivity to dentin demonstrated in this study, tetracycline HCl has been shown to inhibit collagenase activity, and to inhibit in vitro bone resorption (Golub et al. 1984, Gomes, Golub & Ramamurthy 1984); activities which may facilitate periodontal regeneration without adverse effects such as root resorption. All of these effects are likely to be enhanced when tetracycline HCl is available at the site for prolonged periods of time.

Dentin surface morphology after tetracycline HCl conditioning resembles that obtained when citric acid is utilized. Preparation of the dentin with citric acid has been shown to prevent epithelial cell growth and to enhance fibroblast cell growth, conditions which would favor new periodontal attachment.

B. Agents Which Stimulate Formulation of Endothelial Cells.

Such agents cells include fibronectin, Endothelial Cell Growth Factor (ECGF), and Platelet Derived Growth Factor.

Preferred are the use of either fibronectin or ECGF, and the use of ECGF subsequent to fibronectin.

The following examples show that dentin treated with a demineralizing agent and then with a endothelial cell formation stimulating agent have improved new connective tissue attachment.

Materials and Methods

Cell Culture and Culture Conditions

Human gingival epithelial cells and fibroblasts were grown from biopsies of gingival epithelium and connective tissue obtained from normal adult male subjects with healthy periodontal tissue. Epithelial explants were cultured on type IV collagen and laminin coated tissue culture dishes, while connective tissue explants were cultured on type I collagen and fibronectin coated tissue culture dishes. Culture media consisted of NCTC 109 supplemented with 10% fetal bovine serum, nonessential amino acids, sodium pyruvate, gentamycin (250 ug/ml) and 25 mM Hepes buffer. Cells were grown to confluency and passaged using a 1 to 2 split ratio. Third passage cells were used for all experiments.

Attachment Assays and Growth Assays

All dentin blocks were prepared from bovine teeth as previously described (Wikesjo et al. 1985). The top surface of the dentin slab (32 mm$^2$) was used as substrate for cell attachment and growth assays. For attachment assays, 250 ul of a 2.5 mg/ml solution of purified fibronectin was applied to the dentin surface and allowed to remain for 5 minutes. The surface was then flushed with sterile phosphate buffered saline (PBS). Freshly suspended cells ($5 \times 10^3$) were then applied as a drop on the surface of the slab and the slab placed in a chamber of 100% humidity at 37° C. for 2 hours. Slabs were removed, washed in sterile PBS to remove the non-adherent cells and the adherent cells were removed by trypsinization (0.25% trypsin, 0.1% EDTA, 0.2% EGTA) and counted electronically. In separate experiments, cells were labeled with $^{51}Cr$. The numbers of non-adherent and adherent cells were then quantitated by counting total unbound and bound radioactivity.

For growth assays, the applied cell number was adjusted such that the top surface of all dentin slabs had $2.5 \times 10^3$ attached cells after a two hour attachment period. Slabs were placed in 35 mm tissue culture dishes to which Minimal Essential Media plua 10% fetal bovine serum, supplemented with non-essential amino acids, sodium pyruvate, glutamine and gentamycin (500 ug/ml). The medium was changed at eight hour intervals and fresh media was added to the top surface of the slabs. After seven days in culture the attached cells were released by trypsinization and counted electronically.

Preparation of Glycoproteins and Antibodies

Laminin was purified by the method of Timpl, et al., 1979 and Terranova et al., 1980, which is briefly as follows. The protein was extracted from EHS mouse tumor with 0.5M NaCl. The extract was chromatographed twice using DEAE cellulose in 2.0M Urea, 0.5M NaCl, pH 7.4, and the unbound material was collected. This was passed over an A5M agarose column. The laminin obtained showed only the two expected bands (200 and 400KD) when subjected to gel electrophoresis under reducing conditions. The laminin obtained from the A5M agarose column was passed over a PDP-10 polyacrylamide gel filtration column to ensure its separation from low molecular weight contaminants.

The serum fibronectin is isolated by affinity chromatography under nondenaturing conditions (Mossesson and Unfleet, 1970; Engvall and Rouslahti, 1977; Vuento and Rouslahti, 1979). Briefly, disposable columns (BioRad Labs) are packed with 36 ml immobilized gelatin (Pierce Chem.) and then washed with 0.1% sodium azide in phosphate buffered saline. The columns are then extensively washed with 0.15M NaCl, 10mM TRIS, 5mM EDTA, pH 7.4, after which 150 ml of plasma are applied. This is allowed to stand for 2 hours at 4° C. after which the columns are washed with 0.5M NaCl, 10mM TRIS, 5mM EDTA, pH 7.4. The bound fibronectin is eluted with 4M urea, 10mM TRIS. This is extensively dialized against MEM at 4° C. and prepared in a sterile, nontoxic fashion for use in phosphate buffered saline (PBS).

Since only one column is being used per patient, no risk of cross-contamination is foreseen. Also, all solutions are sterile filtered through 0.22 micron pore filters.

Iodination is by the Lactoperoxidase method. Purified protein is iodinated with $^{125}I$ using the Lactoperoxidase method. Briefly, 2–5 ug purified protein is added to 50 ml of 0.1 M phosphate buffer. To this, 0.5mCi Na$^{125}$I (NEN) is added along with 50 ul of Enzymobeads (Amersham) and 20 ul of glucose solution (1.8% in PBS). The reaction mixture is incubated 5 minutes at room temperature and then terminated by centrifuging the beads at 10,000 RPM for 1 minute. The labelled pure protein is then diluted with unlabelled pure protein.

Binding Studies

Dentin slabs were preincubated in various concentrations of tetracycline HCl and then washed for five minutes in 5.0 ml of cold phosphate buffered saline (PBS). The slabs were then immersed for 5 minutes in 500 ul of labeled glycoprotein (adjusted to give $2 \times 10^6$ CPM/ml) at 37° C. Slabs were then washed in 5.0 ml PBS, dissolved in 5.0 ml of 2N HCl and a 100 ul aliquot counted. In other experiments, slabs previously treated with 100 mg/ml tetracycline HCl, saturated citric acid and control were used as substrate for binding of $^{125}$I-fibronectin. Slabs were immersed in various concentrations of $^{125}$I-Fibronectin for 5 minutes at 37° C. and then washed with cold phosphate buffered saline (PBS). Adsorbed counts were then quantitated by gamma counting after dissolving the slabs in 5.0 ml of 2N HCl.

RESULTS

When $^{125}$I-laminin and $^{125}$I-fibronectin were examined for their ability to bind to control dentin slabs, we observed a greater binding of laminin. Tetracycline HCl preparation (5 minute exposure, followed by a 5 minute rinse in 5 ml of PBS) reversed the pattern of binding at immersion concentrations as low as 10 mg/ml. Maximal binding of fibronectin was achieved when the dentin slabs were immersed in tetracycline HCl at concentrations of 100 mg/ml and above. Conversely, laminin binding was decreased when 1.0 to 10.0 mg/ml of tetracycline HCl was used. At tetracycline HCl treatment levels above 25 mg/ml the amount of laminin bound to the slab remained constant. Using slabs either conditioned with 100 mg/ml tetracycline HCl, citric acid and control (PBS) the amount of adsorbed fibronectin varied in a dose dependent manner. More than 50 ug/slab of bound fibronectin was achieved by incubation of tetracycline HCl prepared slabs in 2.5 mg fibronectin/ml PBS. These results correspond directly to the ability of the tetracycline HCl prepared-fibronectin treated (TTC-FN) slabs to bind fibroblasts.

The ability of epithelial cells and fibroblasts to attach to dentin slabs was used as a test of substrate preference. When untreated (control) slabs were used, epithelial cells attached to a greater extent than fibroblasts (four-fold increase). The numbers of attached epithelial cells and fibroblasts were also measured on dentin slabs prepared with varying concentrations of tetracycline HCl and preincubated with a constant concentration of fibronectin (2.5 mg/slab). We found a reversal in substrate preference when tetracycline HCl and fibronectin were used to condition the dentin slabs. Tetracycline HCl and fibronectin conditioning produced a four-fold increase in the number of attached fibroblastic cells over untreated dentin slabs. Furthermore, 50 mg/ml tetracycline HCl and fibronectin conditioning significantly inhibited epithelial cell attachment.

The addition of affinity purified antibody directed against laminin was shown to inhibit 80% of the epithelial cell attachment to untreated slabs. Affinity purified antibody directed against fibronectin, inhibited 90% of the fibroblast attachment to TTC prepared slabs. Neither antibody produced effects when the alternate cell type was used.

In a separate experiment, cells were initially preincubated for 4 hours in 25 ug/ml cycloheximide to inhibit endogenous protein synthesis. In the absence of added exogenous glycoprotein, minimal cell attachment was observed. In the presence of added exogenous glycoprotein (5 ug/ml) specific for the cell types employed, both epithelial cells and fibroblasts showed rapid attachment to dentin slabs prepared for the specific cell types.

When citric acid, or control slabs were compared to tetracycline HCl-prepared slabs, human gingival fibroblasts attached more rapidly and to a greater extent to tetracycline HCl prepared dentin surfaces. After a 30 minute attachment period, tetracycline HCl prepared dentin slabs bound three times more fibroblasts than citric acid prepared slabs, and seven times more fibroblasts than control dentin slabs. We also examined the rate and degree of attachment of epithelial cells to treated dentin slabs. Both citric acid and tetracycline HCl preparations led to a substantial reduction in the rate of epithelial cell attachment. After a 2 hours attachment assay, tetracycline-fibronectin-prepared slabs acted as poor substrate for epithelial cells when compared to control slabs.

We next examined the growth of epithelial cells and fibroblasts on dentin slabs either untreated (control), citric acid-fibronectin prepared, or conditioned by immersion in tetracycline HCl at 10 mg/ml and 100 mg/ml followed by 2.5 mg/slab fibronectin application. After seven days in culture, we observed that epithelial cells proliferated significantly better than fibroblasts when control dentin slabs are used as substrate. In contrast, with either citric acid or tetracyclic HCl preparation, this tendency could be reversed. When dentin slabs are conditioned with 100 mg/ml tetracycline HCl, the growth of fibroblasts was increased seven-fold over that observed with epithelial cells.

The Kit

The invention further relates to a kit comprised of the following:

(a) tetracycline or a pharmaceutically acceptable salt thereof in a pharmaceutically acceptable dosage form for administration to teeth; and (b) fibronectin in a pharmaceutically acceptable dosage form for administration to the teeth.

The kit can further comprise or have substituted for the fibronectin, Erdothelial Cell Growth Hormone, a pharmaceutically acceptable dosage form for administration to the teeth.

Preferably, the tetracycline will be administered as an aqueous solution at a dosage of 25-200 mg/ml.

Preferably, the fibronectin will be administered as an aqueous solution at a dosage of 2-10 mg/ml.

Preferably, the Endothelial Cell Growth Hormone will be administered as an aqueous solution at a dosage of 1-10 microgram/ml.

Particularly envisioned by the inventors is a kit comprised of:

(a) tetracycline HCl 500 mg;
(b) 10 ml sterile pyrogen-free distilled water;
(c) fibronectin - 10 mg;
(d) two 5 ml syringes;
(e) 100 ml sterile PBS; and
(f) one 25 ml syringe.

The Method

The method preferably used by the periodontal surgeon would be as follows:

(a) exposing periodontal area requiring treatment by methods known to the surgeon to produce a flap;

(b) applying a tetracycline salt at a dose of 25-200 mg/ml to the exposed area;

(c) allowing the tetracycline salt to have contact with the treated area for 1-10 minutes;

(d) flushing the treated area;

(e) applying fibronectin at a dose of 2-10 mg/ml to the treated area for at least 4 minutes;

(f) optionally flushing the treated area;

(g) optionally applying Endothelial Cell Growth Factor at a dose of 1-10 microgram/ml in addition to or instead of the step of applying fibronectin; and (h) repositioning the flap and suturing.

Particularly preferred would be the following:

After elevation of the mucoperosteal flaps and removal of all granulation tissue and local factors, the area is flushed with PBS and dried with cotton 2×2 sponges. Tetracycline HCl is applied using a drop technique from one of the 5 ml syringes. The tetracycline HCl is allowed to remain in contact with the tooth surface for about 5 minutes. PBS is used to flush the area. Fibronectin (1 mg/ml) is then applied to the same area using the drop technique. After 5 minutes of incubation on the tooth surface, the flaps are repositioned, sutured and covered with periodontal wound dressing.

What is claimed is:

1. A method of promoting periodontal regeneration and fibroblast bonding in humans, wherein the method comprises (a) exposing periodontal area requiring treatment by methods producing a flap;

(b) applying a tetracycline salt at a dose of 25-200 mg/ml to the exposed area to be treated;

(c) allowing the tetracycline salt to have contact with the treated area for 1-10 minutes;

(d) flushing the treated area;

(e) drying the treated area;

(f) applying fibronectin at a dose of 2-10 mg/ml to the treated area for at least 4 minutes;

(g) optionally flushing the treated area;

(h) optionally applying Endothelial Cell Growth Factor at a dose of 1-10 microgram/ml; and (i) repositioning the flap and suturing.

2. A method of promoting periodontal regeneration and fibroblast bonding in humans, wherein the method comprises (a) exposing periodontal area requiring treatment by methods producing a flap;

(b) applying a tetracycline salt at a dose of 25-200 mg/ml to the exposed area to be treated;

(c) allowing the tetracycline salt to have contact with the treated area for 1-10 minutes;

(d) flushing the treated area;

(e) applying Endothelial Cell Growth Factor at a dose of 1-10 microgram/ml; and (f) repositioning the flap and suturing.

* * * * *